(12) United States Patent
Bian et al.

(10) Patent No.: US 10,576,159 B2
(45) Date of Patent: Mar. 3, 2020

(54) METHOD FOR PREPARING AN INDUCED OSTEOGENESIS FORMULATION

(71) Applicant: Zhejiang Shanshi Medical Device Co., Ltd., Zhejiang (CN)

(72) Inventors: Junjie Bian, Zhejiang (CN); Xiaohuan Bi, Zhejiang (CN)

(73) Assignee: Zhejiang Shanshi Medical Device Co., Ltd., Hangzhou (CN)

( * ) Notice: Subject to any disclaimer, the term of this patent is extended or adjusted under 35 U.S.C. 154(b) by 101 days.

(21) Appl. No.: 15/619,705

(22) Filed: Jun. 12, 2017

(65) Prior Publication Data

US 2017/0354740 A1    Dec. 14, 2017

(30) Foreign Application Priority Data

Jun. 13, 2016 (CN) .......................... 2016 1 0410872
Jun. 13, 2016 (CN) .......................... 2016 1 0420637
Jun. 13, 2016 (CN) .......................... 2016 1 0421785

(51) Int. Cl.
| | |
|---|---|
| *A61K 47/42* | (2017.01) |
| *A61K 38/18* | (2006.01) |
| *A61K 35/32* | (2015.01) |
| *A61K 47/64* | (2017.01) |
| *A61K 38/00* | (2006.01) |
| *C07K 14/51* | (2006.01) |
| *A61K 38/16* | (2006.01) |

(52) U.S. Cl.
CPC .............. *A61K 47/64* (2017.08); *A61K 35/32* (2013.01); *A61K 38/00* (2013.01); *A61K 38/1875* (2013.01); *C07K 14/51* (2013.01); *A61K 38/16* (2013.01); *A61K 38/18* (2013.01)

(58) Field of Classification Search
None
See application file for complete search history.

(56) References Cited

U.S. PATENT DOCUMENTS

2006/0177387 A1    8/2006  Slavin et al.
2007/0254040 A1   11/2007  Scaffidi et al.

FOREIGN PATENT DOCUMENTS

CN         102258062 A  * 11/2011

OTHER PUBLICATIONS

Murata, "Bone Engineering Using Human Demineralized Dentin Matrix and Recombinant Human BMP-2", Journal of Hard Tissue Biology, vol. 14, pp. 80-81. (Year: 2005).*
Kim et al., "Effects of Demineralized Dentin Matrix Used as an rhBMP-2 Carrier for Bone Regeneration", Journal of Hard Tissue Biology, vol. 23, pp. 415-422. (Year: 2014).*
Bessho et al., "Human Dentin-matrix-derived Bone Morphogenetic Protein", Journal of Dental Research, vol. 70, pp. 171-175. (Year: 1991).*
Freshney, Culture of Animal Cells, 6th Edition; John Wiley & Sons, Inc.: Hoboken, NJ; Chapter 8; pp. 99-101. (Year: 2010).*
Urist et al., "Solubilized and insolubilized bone morphogenetic protein", Proc. Natl. Acad. Sci. USA, vol. 1828-1832 (Year: 1979).*
European Search Report issued in EP 17175408.8 dated Oct. 26, 2017.
Um et al. (Jan. 2016) "Demineralized dentin matrix combined with recombinant human bone morphogenetic protein-2 in rabbit calvarial defects", Journal of the Korean Association of Oral and Maxillofacial Surgeons, 42(2):90-98.
Block et al. (Jan. 1995) "Does Xenogeneic Demineralized Bone Matrix Have Clinical Utility As A Bone Graft Substitute?" Medical Hypothesis 45(1):27-32.
Mizutani et al. (1996), "A Study of the Bone Morphogenetic Protein Derived from Bovine Demineralized Dentin Matrix", Naboya J. Med. Sc. 59:37-47.

* cited by examiner

*Primary Examiner* — Michelle F. Paguio Frising
(74) *Attorney, Agent, or Firm* — Lathrop GPM LLC

(57) ABSTRACT

The application is related to a method for preparing an induced osteogenesis formulation, the method comprises the following steps: (1) a human dental matrix is decalcified; (2) then an exogenous active protein BMP, i.e. bone morphogenetic protein is added to the decalcified dental matrix, resulting in the induced osteogenesis formulation.

4 Claims, 2 Drawing Sheets

METHOD FOR PREPARING AN INDUCED OSTEOGENESIS FORMULATION

RELATED APPLICATIONS

This application claims priority to CN 201610410872.4, filed Jun. 13, 2016; CN 201610420637.5, filed Jun. 13, 2016 and 201610421785.9, filed Jun. 13, 2016, each of which are incorporated herewith in their entirety.

TECHNICAL FIELD

The present invention relates to a formulation for repairing bone damage, particularly it relates to a formulation and method for induced osteogenesis, promoting bone tissue formation or repairing bone damage.

BACKGROUND OF THE INVENTION

Induced osteogenesis technology is an usual technology for current surgical repair and periodontal reconstruction, it is mainly to produce new bone by activating bone growth and production function using osteoinductive factor. There are many osteoinductive factors, at present the researches are mainly focused on bone morphogenetic protein (bone morphogenetic protein, BMP) family proteins, the bone morphogenetic protein belongs to low-molecular weight glycoproteins, multiple protein compositions of Bone morphogenetic protein 1 to 14 has been found, wherein the osteoinductive activity of bone morphogenetic protein-2 is strongest, the other bone morphogenetic protein compositions have a synergistic effect with the bone morphogenetic protein-2, participating in the induced osteogenesis process together. Some scholars consider that the bone morphogenetic protein is one of a transforming growth factor-13 (TGF-13) superfamily, it has a marked capability of bone regeneration and osteointegration, it is able to induce formation of cartilage and bone, and it is able to induce transformation of mesenchymal cell around the blood vessel into bone marrow stem cell, the bone morphogenetic protein formed by its interaction with extracellular matrix macromolecule is the basis for adjusting bone formation. The bone morphogenetic protein is widely present in the bone matrix and dental matrix of mammals, it is an acid glycoprotein without species specificity and belongs to local growth factor, but the bone morphogenetic protein in the bone gradually reduces with the age, while reduction of the bone morphogenetic protein in the dental matrix is not seen. Other researches show that the crude extracts of the bone morphogenetic protein in the decalcified bone matrix (DBM) are 10 folds of those in the decalcified dental matrix (DDM) with the same mass, accordingly the induced osteogenesis amount of the decalcified dental matrix in muscle should be 10 folds of that in the decalcified bone matrix with the same mass. But, the bone morphogenetic protein alone diffuses too fast in the body, it is also easy to be broken down by a proteinase, thus it cannot act on more target cells within an effective time, its inductive activity is difficult to be fully achieved; purification and preparation of the bone morphogenetic protein is difficult, and its cost is high, so it is difficult to be widely used in clinical practice; some studies find that the bone morphogenetic protein with high purify cannot obtain high biologically inductive activity, only if being used in combination with the corresponding bone matrix, it can effectively induce osteogenesis, it is because the collagen and the matrix may affect calcium and phosphate ions in hydroxyapatite crystal, the organic substance may also serve as a center for crystallization. Despite there are many reports on carrier for the bone morphogenetic protein, such as using hydroxyapatite, tricalcium phosphate, polyester, collagen, demineralized bone matrix, titanium dioxide, blood clot etc., the binding mode, compounding method, and compounding ratio between the bone morphogenetic protein and the carrier have no consistent conclusion. Therefore, current research direction is transferred to developing a composite osteoinduction material.

Researches consider that the decalcified dental matrix (DDM) is a composite being rich in bone morphogenetic protein, collagen and other proteoglycans, it is a novel bioactive material having an osteoinductive effect with human homology, it is rich in multiple composites of bone inducing protein with its carrier, resulting in a natural slow-delivery system for the bone morphogenetic protein. For example, China Invention Patent 95112416.1, or China Invention Patent Application, Application No. 201310602830.7, Application No. 201310602878.8 disclose that these materials being able to promote wound healing or regeneration of bone are obtained by treatment of tooth. In addition, some compositions may also be added into the dental matrix, to further improve the effect of the dental matrix; for example, such as described in China Invention Patent Application, Application No. 201510089391.3 and Application No. 201110129457.9.

Of courses, there is also a method of in vitro expression of BMP protein then mixed with bone powder or other powder, the actual effect of the repair material prepared by such a method is no ideal, it is mainly because the BMP protein is easy to loss its activity in vitro, it is added into damaged bone after being mixed with these powders, thus it is easy to be degraded by enzymes and also loss its activity. Therefore, only if the activity of BMP is maintained in vivo, growth of the bone tissue can be promoted more effectively.

For the above-described method, despite it has a certain effect on repair of bone damage, there are many inherent defects yet, they are mainly in the flowing aspects: (1) teeth as the source of the active BMP are limited, they cannot meet the growing market demand, because using the dental matrix as the raw material restricts the development of industry; (2) after the tooth and bone are pulverized, they are usually decalcified in a acidic solution, to obtain a powder containing active protein BMP, but treatment by acid and base can release the calcium ion and expose the BMP protein, meanwhile having great damage to BMP protein, it is because BMP is easy to be denaturated in an acidic condition and loss activity; this reduces utilization efficiency of the BMP protein.

Therefore, it is necessary to improve the current method, or to adopt a new method to obtain the bone repair material.

SUMMARY OF THE INVENTION

In one respect, the present invention provide a method for preparing induced osteogenesis formulation, the method comprises the following steps: 1. a dental matrix is decalcified; 2. then an exogenous active protein BMP, i.e. bone morphogenetic protein, is added into the decalcified dental matrix, resulting in the induced osteogenesis formulation.

In another aspect, the present invention provide a method for preparing bone induced osteogenesis formulation, this method comprises the following steps: 1. two parts of dental matrix is decalcified; 2. then the bone morphogenetic protein is removed from the two parts of the decalcified dental matrix; 3. finally the extracted bone morphogenetic protein is mixed with one part of the decalcified dental matrix, resulting in induced osteogenesis formulation.

In a further aspect, the present invention provides a method for preparing an induced osteogenesis formulation, the method comprises the following steps: 1. an exogenous bone matrix is decalcified; 2. then protein is removed from the decalcified bone matrix; 3. the exogenous bone morphogenetic protein is mixed with bone matrix treated in step (2), the induced osteogenesis formulation is formed by the exogenous protein and the bone matrix.

In some preferred embodiments, a method for decalcifying human tooth comprises the following steps: (1) the tooth tissue is pulverized into granule or lyophilized powder by a mechanical method; (2) the tooth tissue granule or lyophilized powder is put in a 0.65 to 0.72 N hydrochloric acid solution, and immersed at 36° C. for 12 hours to complete the decalcification; (3) the decalcified product is dried at low temperature to obtain a lyophilized powder.

Preferably, the lyophilized powder is immersed in 3% hydrogen peroxide at 35° C. for 30 minutes to obtain a decalcified human dental matrix.

Preferably, said human dental matrix lyophilized powder or particle is put in a 70% ethanol solution at 5° C. and stored for use.

Preferably, the decalcified human dental matrix particle is put in ethanol solution and stored for use. Wherein, the concentration of ethanol is any concentration, e.g., 70%, 60%, 50%, 75%, 78%, 80%, 85% or 95%.

In preferred embodiments, firstly the raw material teeth are immersed and disinfected with a 50% disinfectant (for example, containing 1.2% active component sodium hypochlorite), the immersion and disinfection time is 45 minutes, the temperature is 36° C.; the useless parts on the tooth are removed by a mechanical method; the tooth tissue pulverized into granule or lyophilized powder is immersed and disinfected with 1.2% sodium hypochlorite, the immersion and disinfection time is 45 minutes, the temperature is 36° C. Then, the teeth are pulverized.

The teeth used herein may be either human teeth or tooth of any mammals. Human teeth are preferred.

In some preferred embodiments, an exogenous BMP protein is added into the decalcified tooth matrix, the method for adding the exogenous protein is as follows: firstly the decalcified dental matrix powder is suspended in a phosphate buffer of PH=6.0 to 7.5 (100 g for preparation of 1 L buffer solution), then the exogenous BMP is dissolved in the same phosphate buffer with PH=6.0 to 7.5 (its concentration is 1.0 M), then mixed together, and placed into an agitator for uniform and slow agitation, the agitation rate is 12 to 120 Rotation Per Minute, meanwhile agitated at room temperature for 12 to 24 hours, during agitation the protein concentration of BMP in the mixed solution is detected every 3 hours, agitation is stopped until the concentration decreases below 20% to 35% of the initial BMP concentration (0.2 to 0.35 M), then centrifuged, the supernatant is removed, the remaining powder is filtered, then dried at low temperature to obtain a human dental matrix, and put in a 70% ethanol solution at 5° C. and stored for use.

In some preferred embodiments, two parts of the human dental matrix is decalcified, then protein is extracted from the decalcified matrix, then the extracted BMP protein is mixed with one part of human dental matrix. The treatment method is: firstly the extracted dental matrix powders after decalcification and deproteinization (BMP active protein and/or other impurity proteins) are suspended in a phosphate buffer of PH=7.0 (120 g for preparation of 1 L buffer solution), then an exogenous BMP (BMP protein extracted from the two parts of matrix) is dissolved in a phosphate buffer (PH=7.0), then the two buffer solutions are mixed together, and placed into an agitator for uniform and slow agitation, the agitation rate is 15 to 120 Rotation Per Minute, meanwhile agitated at room temperature for 12 to 24 hours, during agitation the concentration of the BMP protein in the mixed solution is detected every 3 hours, the agitation is stopped until the concentration decreases below 20% to 35% of the initial BMP concentration, then centrifuged, the supernatant is removed, the remaining powder is filtered, then dried at low temperature to obtain the human dental matrix. Preferably, the human dental matrix is put in an ethanol solution at 5° C. and stored for use.

In some preferred embodiments, fresh exogenous bones (human bone or mammal bone) (the human bone used herein are mainly human bone removed from patient's body by a doctor or donated fresh human bone) are decalcified, the method for decalcifying treatment is as follows: the bone tissue is pulverized into granule or lyophilized powders by a mechanical method; (2) the granule or lyophilized powders made from bone are put in a 0.65 to 0.72 N hydrochloric acid solution, and immersed at 36° C. for 24 to 48 hours to complete the decalcification; (3) the decalcified product is dried at low temperature to obtain a decalcified bone powder or particle. Then, immersed in 3% hydrogen peroxide at 35° C. for 30 minutes to obtain a decalcified matrix; or, said matrix is put in an ethanol solution at 5° C. and stored for use. Preferably, the decalcified product of human dental matrix particle is put in an ethanol solution and stored for use. Wherein, the concentration of ethanol is any concentration, e.g., 70%, 60%, 50%, 75%, 78%, 80%, 85% or 95%.

Then, the decalcified bone powder is deproteinated, the process for deproteinization is as follows: an appropriate amount of water is added into the decalcified bone powder, and heated in a water bath kettle for 56 to 72 hours, the temperature was 35 to 40° C., then centrifuged, the supernatant is removed, BMP protein is extracted from the supernatant, and the concentrate and impurity proteins are removed. Or, bone powder is added to a buffer solution of pancreatin or papain, and treated at 37 to 40° C. for 3 to 4 days or more, then centrifuged and the supernatant is removed, the protein is broken down by enzyme treatment, the precipitate after centrifugation is retained, providing a deproteinated bone powder.

Preferably, the decalcified and deproteinated bone powder is mixed with the exogenous BMP protein, the step of the treatment is as follows: firstly the bone powder after decalcification and BMP protein extraction is suspended in phosphate buffer of PH=7.0 (120 g/L), then an exogenous BMP is dissolved in a phosphate buffer (1.2 M), then the two solutions are mixed together, put in a n agitator for uniform and slow agitation, the agitation rate is 30 to 80 Rotation Per Minute, meanwhile agitated at room temperature or 25 to 30° C. for 12 to 24 hours, during agitation the protein concentration of BMP in the mixed solution is detected every 3 hours, the agitation is stopped until the concentration decrease below 20% to 25% of the initial BMP concentration (0.24 to 0.25 M), then centrifuged, the supernatant is removed, the remaining powder is filtered, then dried at low temperature to obtain a matrix. Preferably, put in 70% ethanol solution at 5° C. and stored for use.

Preferably, the exogenous BMP protein is BMP-2, BMP-4, and BMP-7 (Shanghai Wheat Warehouse Biological Technology Co., Ltd). Preferably, the exogenous BMP protein is BMP-2. Or, preferably, said exogenous BMP protein is one or more of BMP-2, BMP-1, BMP-3, BMP-4, BMP-5, BMP-6 or BMP-7. These commercial BMP active proteins all can be purchased commercially.

The powder or formulation used herein are all lyophilized powder or formulation in other forms. The formulation and reagent, composition or substance used herein have an identical meaning.

BENEFICIAL EFFECT

Figure 1:
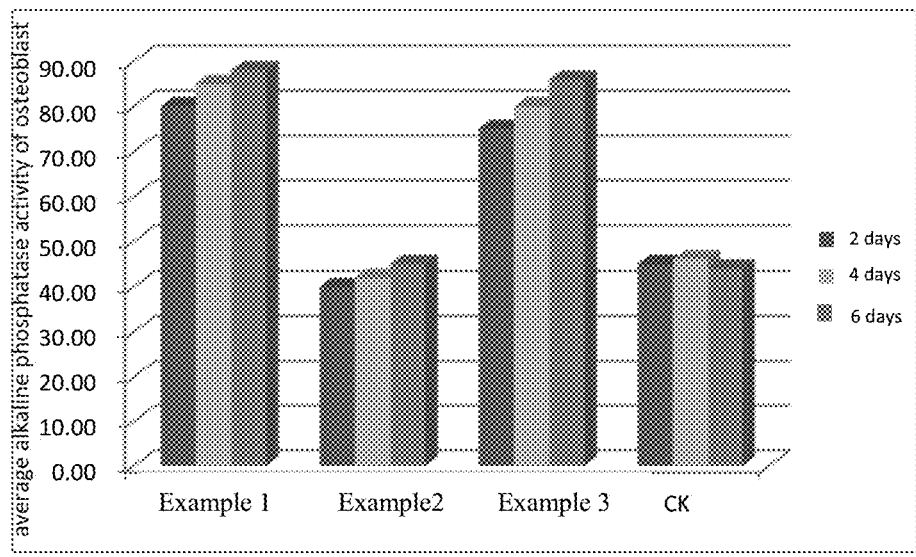
FIG. 1 is a diagram of comparison results of effects on osteoblast proliferation of Example 1 to 3 with a control CK.

The formulations for promoting bone tissue growth or repair provided by the present invention has a equivalent effect to the conventional human dental matrix, some of them are better than the existing human dental matrix, thereby providing some alternative products, and reducing product cost, and meeting the growing market demand.

DETAILED DESCRIPTION OF THE EMBODIMENTS

Example 1: Decalcification Treatment of Human Dental Matrix and Addition of Exogenous BMP Protein 1. The step for decalcifying human dental matrix is as follows:

(1) Collected human teeth were placed into a container with clean water, stored at a temperature below 5° C.;

(2) Raw material teeth were immersed and disinfected with 1.2% sodium hypochlorite, the time was 55 minute, and the temperature was 30° C. (or other temperatures, e.g., 35, 30, 38, 40° C.);

(3) Useless parts on the teeth were removed;

(4) The tooth tissue was pulverized into granule or lyophilized powder by a mechanical method, the average particle diameter was 0.25 mm (e.g., 0.2, 0.5, 0.6, 0.7, 0.8, 1.0, 1.2 mm);

(5) The tooth tissue pulverized into granule or lyophilized powder was immersed and disinfected with 1.2% sodium hypochlorite, the immersion and disinfection time was 45 minutes, the temperature was 35 to 40° C.;

(6) The tooth tissue granule or lyophilized powder was put in a 0.65 (or 0.67, 0.68, 0.67, 0.72) N hydrochloric acid solution, and immersed at 38° C. for 16 hours to complete the decalcification;

(7) Dried at low temperature, and immersed in a 3% hydrogen peroxide at 35° C. for 30 minutes. Through detection, the dental matrix granule or lyophilized powder decalcified by this method was fine and uniform, the morphology was consistent, being in a shape of round bar, the length was about 100 to 200 nm, and the diameter was about 50 to 100 nm.

2. Addition of exogenous BMP protein.

a. To 1000 g of the tooth matrix decalcified in step (7) an exogenous BMP protein was added, the method for adding the exogenous protein is as follows:

b. Firstly the hydrogen peroxide was removed from the dental matrix decalcified in step (7), and washed with sterile water for many times until no hydrogen peroxide was present, to obtain 100 g of human dental matrix powder;

c. Then the decalcified dental matrix powder was suspended in 1 L phosphate buffer of PH=7.2;

d. An exogenous BMP-2 (1.0 g, purchased from Shanghai Wheat Warehouse Biological Technology Co., Ltd) was dissolved in the phosphate buffer PH=7.2 of same volume, then the two buffer solutions were mixed together, and placed onto an agitator for uniform and slow agitation, the agitation rate was 30 to 80 Rotation Per Minute, meanwhile being in a water bath kettle with a varying temperature, the temperature sequence was as follows: 26° C., 8 hours; 30° C., 6 hours; 28° C., 8 hours; 28° C., 12 hours; then kept at a constant temperature of 30° C. and the agitation was continued, the protein concentration of BMP-2 in the mixed solution was detected every 3 hours, until the concentration decreased below 20% to 25% of the initial BMP-2 concentration and agitation was stopped, then centrifuged, the supernatant was removed, the remaining powder was filtered, then dried at low temperature to obtain a lyophilized powder of human dental matrix. Through detection, the dental matrix granule or lyophilized powder decalcified by this method was fine and uniform, the morphology was consistent, being in a shape of round bar, the length was about 100 to 220 nm, and the diameter was about 40 to 110 nm.

Example 2: Decalcification Treatment of Human Dental Matrix and Addition of Exogenous BMP Protein The difference with Example 1 is that the exogenous protein is BMP-7, and the other conditions are all same.

Example 3: Decalcification Treatment of Human Dental Matrix and Addition of Exogenous BMP Protein The difference with Example 1 is the mixed buffer solution was in a water bath kettle of constant temperature, the temperature was 15, 20, 35, 38° C., the time was 34 hours or more, the protein concentration of BMP-2 in the mixed solution was detected every 3 hours, the agitation was stopped until the concentration decreased below 20% to 25% of the initial BMP-2 concentration, then centrifuged, the supernatant was removed, the remaining powder was filtered, then dried at low temperature obtain the human dental matrix, put in 70% ethanol solution at 5° C. and stored for use. Through detection, the dental matrix granule or lyophilized powder decalcified by this method was fine and uniform, the morphology was consistent, being in a shape of round bar, the length was about 100 to 220 nm, and the diameter was about 40 to 110 nm.

Example 4: Decalcification and Deproteinization (BMP) Treatment of Two Parts of Human Dental Matrix, Mixing of Extracted BMP Protein with One Part of Decalcified and Deproteinized Human Dental Matrix Powder 1. The step for decalcifying human dental matrix is as follows:
(1) Collected human teeth were put in a container with clean water, stored at a temperature below 5° C.;
(2) Raw material teeth were immersed and disinfected with 1.2% sodium hypochlorite, the time was 55 minutes, and the temperature was 30° C. (or other temperatures, e.g., 35, 30, 38, 40° C.);
(3) Useless parts of the teeth were removed;
(4) The tooth tissue was pulverized into granule or lyophilized powder by mechanical method, the average particle diameter was 0.25 mm (e.g., 0.2, 0.5, 0.6, 0.7, 0.8, 1.0, 1.2 mm);
(5) Then the tooth tissue pulverized into granule or lyophilized powder was immersed and disinfected with 1.0% sodium hypochlorite, the immersion and disinfection time was 45 minutes, and the temperature was 35 to 40° C.;
(6) The tooth tissue granule or lyophilized powder was put in a 0.65 (or 0.67, 0.68, 0.67, 0.72) N hydrochloric acid solution, and immersed at 38° C. for 20 hours to complete the decalcification;
(7) Dried at low temperature, then immersed in 3% hydrogen peroxide at 35° C. for 30 minutes.

2. Extraction treatment of BMP protein.
A protein extraction treatment was conducted to 1000 g powder of the dental matrix decalcified in step (7), the method for extracting BMP protein is as follows:
a. Firstly hydrogen peroxide was removed from the dental matrix decalcified in step (7), and washed with sterile water for many times until no hydrogen peroxide was present, to obtain 1000 g of human dental matrix powder;
b. Then 1000 g of the decalcified dental matrix powder was suspended in 5 L phosphate buffer of PH=7.2;
c. The phosphate buffer of step (b) was heated in the water bath kettle for 280 hours, the temperature was 40° C., during the heat treatment the buffer was continually agitated; then centrifuged, the supernatant was separated from the precipitate, the target protein was isolated from the supernatant by a molecular sieve then purified and concentrated, finally a active extract of BMP protein was obtained, through detection, its molecular weight was 20 to 50 kda. The precipitated powder was filtered, dried, recovered, to obtain 980 g deproteinated dental matrix powder.
d. The decalcified and deproteinated dental matrix powder was mixed with the extracted BMP protein, the step of the treatment is as follows:
Firstly, the dental matrix powder after decalcification and BMP protein extraction was suspend in a phosphate buffer of PH=7.0 (100 g/L, preparing 5 L solution, totally 500 g), then the BMP protein extracted from 1000 g human dental matrix (step c) was dissolved in a phosphate buffer, then the two buffer solutions were mixed together, and placed onto the agitator for uniform and slow agitation, the agitation rate was 30 to 80 Rotation Per Minute, meanwhile agitated at room temperature or 25 to 30° C. for 12 to 24 hours, during agitation the protein concentration of BMP in the mixed solution was detected every 3 hours, the agitation was stopped until the concentration decreased below 10% to 15% of the initial BMP concentration, then centrifuged, the supernatant was remove, the remaining powder was filtered, then dried at low temperature to obtain a matrix, put in a 70% ethanol solution at 5° C. and stored for use.

Through detection, the dental matrix granule or lyophilized powder decalcified by this method was fine and uniform, the morphology was consistent, being in a shape of round bar, the length was about 80 to 180 nm, and the diameter was about 30 to 70 nm.

Example 5: Decalcification and Deproteination Treatment of Exogenous Human Bone and Addition of Exogenous BMP Protein 1. The step for decalcifying human bone is as follows:
(1) Collected human bone was put in a container with clean water, and stored at temperature below 5° C.;
(2) The raw material bone was immersed and disinfected with a 2.0% sodium hypochlorite, the time was 55 minutes, and the temperature was 37° C. (or other temperature, e.g., 35, 30, 38, 40° C.);
(3) Useless parts on the bone were removed;
(4) The bone tissue was pulverized into granule by mechanical method, the average particle diameter was 0.25 mm (e.g., 0.2, 0.5, 0.6, 0.7, 0.8, 1.0, 1.2 mm, or other particle diameters, e.g., 50 to 100, 120 to 200 nm);
(5) The pulverized granule was immersed and disinfected with a 1.5% sodium hypochlorite, the immersion and disinfection time was 45 minutes, and the temperature was 35 to 40° C.;
(6) The bone tissue granule was put in a 0.65 (or 0.67, 0.68, 0.67, 0.72) N hydrochloric acid solution, and immersed at 38° C. for 16 hours to complete the decalcification;
(7) Dried at low temperature to obtain a lyophilized powder or particle, and immersed in 3% hydrogen peroxide at 35° C. for 30 minutes.

Through detection, the bone granule or lyophilized powder decalcified by this method was fine and uniform, the morphology was consistent, being in a shape of round bar, the length was about 120 to 240 nm, and the diameter was about 60 to 120 nm.

2. Degradation treatment of BMP protein.
The protein extraction treatment method of 1000 g powder of the bone matrix decalcified in step (7) is as follows:
a. Firstly hydrogen peroxide was removed from the bone matrix decalcified in step (7), washed with sterile water for many times until no hydrogen peroxide was present, to obtain 1000 g of bone matrix powder; then 1000 g decalcified bone powder was suspended in a 2 L phosphate buffer of PH=7.2;
b. In order to make the enzymolysis reaction reach an ideal degree in conjunction with production input cost, pancreatin was chosen in the experiment, the temperature in the enzymolysis kettle was adjusted to 48 to 50° C., 0.35 g pancreatin was added when the pH value was adjusted to 8.5; the reaction time of the enzyme were all 12 to 56 hours, and a protein degradation treatment was conducted; after completion of the treatment, centrifuged, the supernatant was separated from the precipitate, the supernatant was removed, the precipitate was retained and dried, to obtain 900 g of decalcified and deproteinated bone powder.
c. Then, 1000 g decalcified and deproteinated bone powder was suspended in a 5 L phosphate buffer of PH=7.2;
d. An exogenous BMP-2 (1.0 g, purchased from Shanghai Wheat Warehouse Biological Technology Co., Ltd) was dissolved in a phosphate buffer of same volume and PH=7.2, then the two buffer solutions were mixed together, and placed onto the agitator for uniform and slow agitation, the agitation rate was 30 to 80 Rotation Per Minute, meanwhile being in a water bath kettle with a varying temperature, the temperature sequence was as follows: 26° C., 8 hours; 30° C., 6 hours; 28° C., 8 hours; 28° C., 12 hours; then kept at a constant temperature of 30° C. and the agitation was continued, the protein concentration of BMP-2 in the mixed solution was detected every 3 hours, agitation was stopped until the concentration decreased below 5% to 6% of the initial BMP-2 concentration, then centrifuged, the supernatant was removed, the remaining powder was filtered, then dried at low temperature to obtain bone matrix, put in a 70% ethanol solution at 5° C. and stored for use.

Through detection, the bone matrix granule or lyophilized powder decalcified by this method was fine and uniform, the morphology was consistent, being in a shape of round bar, the length was about 122 to 240 nm, and the diameter was about 60 to 110 nm.

Example 6: Effect Verification of Bone Induced Osteogenesis Formulation

1. Materials and Methods
1.1. Experiment Equipments

Enzyme label plate (24-wells, 96-wells), microplate reader (Model 550), electric centrifuge (80-2 Type), cell incubator (Heraeus BB6220 Type), two-way magnetic heating agitator (Jiangsu Jintan Medical Instrument Factory), pH meter (Shanghai Precision Scientific Instrument Co., Ltd.), constant temperature water bath kettle (Jiangsu Jintan Medical Instrument Factory), medical clean bench (Suzhou Purification Equipment Factory).

1.2. Experiment Materials

A parallel-controlled (CK) treatment experiment was carried out for the materials derived from Example 1 to 5 of the present invention and a commercial dental matrix from Shenzhen GMCB Biological Products Development Co., Ltd., standard fetal bovine serum (Hangzhou Sijiqing Biological Engineering Materials Co., Ltd.), DMEM medium (Sigma), 0.25% trypsin (Sigma), Tritonx-100 (Shanghai Sangon Biotech), ALP standard kit (Shanghai Sangon Biotech).

2. Experiment Methods
2.1. Cultivation of MC-3T3 Osteoblast:

MC-3T3 osteoblast was recovered in a conventional medium containing 10% fetal bovine serum, cultured at a condition of 50 ml/L $CO_2$, saturated humidity, 37° C., the medium was changed after 24 hours, after growth to 80%, digested with a 2.5/L trypsin, passaged, and experiments were carried out to the cells of the 3rd to 4th generations.

2.2. Study on Proliferation of MC to 3T3 Osteoblast.

Before experiment, 0.1 gram of the matrix powder of Example 1 to 5 of the present invention and the commercial dental matrix powder from Shenzhen GMCB Biological Products Development Co., Ltd. were weighed and added into the 24-well plate, each sample was added into three wells on average, ultraviolet was irradiated for 30 minutes for sterilization. The cells in logarithmic phase were digested to make a cell suspension, the concentration was adjusted, such that the inoculum density was $1\times10^4$/ml, and added into the 24-well plate, 1 ml per well, cultured under a condition of 50 ml/L $CO_2$, saturated humidity, 37° C. for 2, 4, 6 days, four wells in each culture plate were successively selected, and 160 μl (microliter) of MTT solution was added, the culture was continued for 4 hours, the culture medium was discarded, 1.2 ml DMSO was added, oscillated for 10 minutes, 200 μl (microliter) was put into the 96-well plate, each example was put into three wells on average, an absorbance value was detected at wavelength of 490 nm by ELISA reader, the cell density was estimated using MTT method cell counting standard curve. The above experiment results were analyzed by one-way ANOVA of SPSS statistic software.

Figure 2:
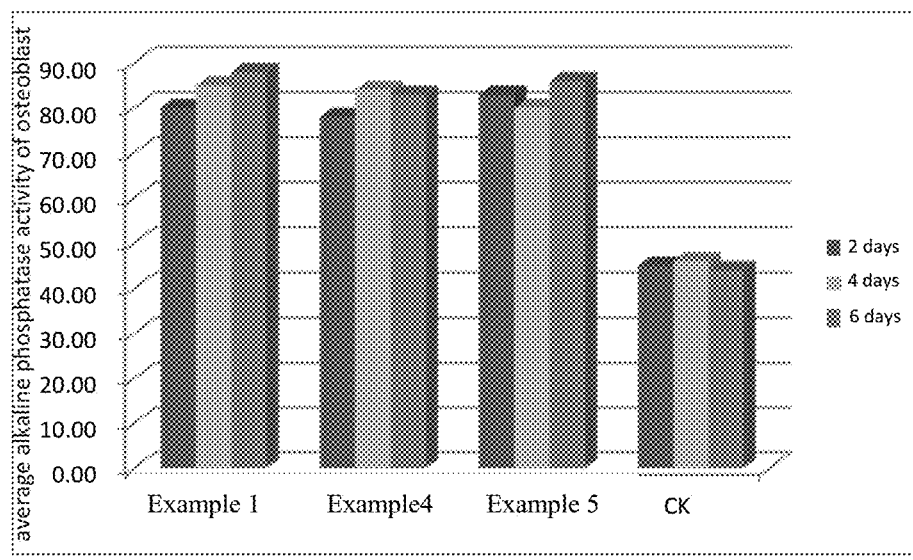
FIG. 2 is a diagram of comparison results of effects on osteoblast proliferation of Example 1, 4, 5 with the control CK.

The results are as follows:

The MTT assay results of different treatments are seen in FIGS. 1 to 2. With the culture time, the cell number in each group is increased. The cell proliferation number in the material inoculated group of Example 1, 3, 4, 5 of the present invention is significantly higher than the control group CK. By statistical analysis, there are statistical differences between the materials in Example 1, 3, 4, 5 and the control CK (P<0.05) (FIG. 1 and FIG. 2). This further demonstrate that the osteogenesis matrix of the present invention obtain has higher activity than the commercial matrix of the prior art, having a great application prospect.

2.3. ALP Activity Assay of MC-3T3 Cell.

The method for cell seeding is same as above, after culture for 2, 4, 6 days, the culture medium was discarded, washed with PBS (0.01 mol/L) 3 times, 800 μl (microliter) of 2 ml/L Triton X was added, placed in a refrigerator at 4° C. over night, then 300 μl ALP substrate was added, kept at 37° C. for 40 minutes, the reaction was stopped by 0.1 mol/L KOH, 200 μl (microliter) was transferred into the 96-well plate, each sample was in three well on average, absorbance A was detected by ELISA reader at 410 nm, i.e., the absorbance A represents activity of cell alkaline phosphatase. In order to eliminate the effect of difference in proliferation rates on the alkaline phosphatase activity, the following correction was carried out: average alkaline phosphatase activity of osteoblast=detected absorbance A value/osteoblast proliferation rate at the same time. The results of the above experiment were analyzed by one-way ANOVA of SPSS statistic software.

Figure 3:
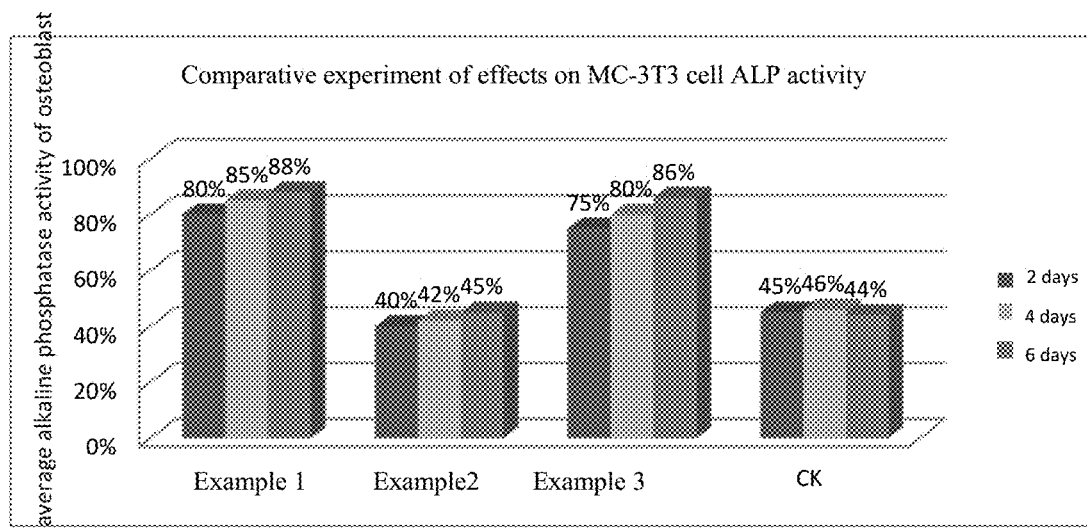
FIG. 3 is a diagram of results of a comparative experiment of effects on MC-3T3 cell ALP activity of Example 1 to 3 with the control CK.
Figure 4:
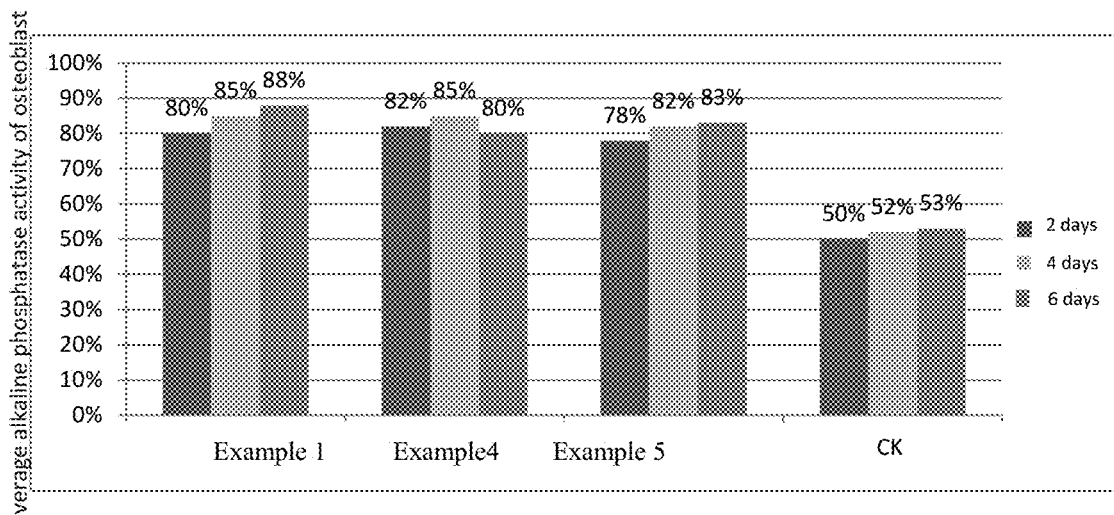
FIG. 4 is a diagram of results of a comparative experiment of effect on MC-3T3 cell ALP activity of Example 1, 4 and 5 with the control CK.

The results are as follows:

Referring to FIGS. 3 and 4. As can be seen from FIG. 3, the activities of the dental matrix obtained in Example 1 and 3 of the present invention are significantly higher than activity of the dental matrix of the prior art. In addition, this also confirms that BMP-2 protein is the main active protein, it plays an important role in bone repair or growth. With the culture time, alkaline phosphatase activities of the cells in each group are all increased, the alkaline phosphatase activities of Example 1 and 3 are higher than those of the control group. By statistical analysis, there are statistical differences (P<0.05) between Example 1 and the control CK, Example 3, 4 and 5 and the control CK, having a significant difference. This further demonstrates that the osteogenesis matrix obtained by the present invention has a higher activity than the commercial matrix of the prior art.

In addition, our additional experiments prove that (the method used is adding exogenous protein as shown in Example 1 and adding exogenous protein as shown in Example 5), among all the exogenous BMP proteins, for example, the exogenous BMP protein is one or more of BMP-2, BMP-1, BMP-3, BMP-4, BMP-5, BMP-6 or BMP-7, when one exogenous protein was used alone, the effect of the exogenous proteins BMP-2, BMP-3 and BMP-7 were better than other proteins.

In addition, we conducted a parallel-controlled (CK) treatment experiment on the matrix particle or dry powder obtain by Example 1, 3, 4, 5 with the commercial dental matrix from Shenzhen GMCB Biological Products Development Co. Ltd., and investigated the repair effect on senile fracture, secondary fracture as well as remoral head necrosis in phase 3 and 4. As a result, it is found that, compared to the existing commercially available dental matrix material (osteogenesis particle or formulation), efficacies of the matrix particle or dry powder in obtain in Example 1, 3, 4, 5 of the present invention are markedly better than current commercial dental matrix material, especially the efficacy of the dental matrix obtained in Example 1, 3, 4 is the best, particularly Example 1 and 4. This may be because that the existing dental matrix material directly undergoes the decalcification treatment, the active protein contained in it is relatively less, and during acidic decalcifying treatment, a great denaturated damage may be caused to the active BMP protein, thus the effect is not ideal, furthermore the decalcification treatment has a large arbitrary, there is large inter-batch differences in the performance of the products. The present invention can significantly improve the efficacy by a simple treatment; in addition, from January 2014 to January 2016, the dental matrix were stored at normal temperature and an activity assay was conducted, the results indicate that after storage at normal temperature for about 2 years, despite the activity was slightly reduced (reduction of about 5 to 10%) (detailed experiment procedure and detailed data are omitted), they maintained high activity after 2 years of storage, its activity is almost 2 to 4 fold of the activity of the current commercial products. This provides a new approach for large-scale standardized commercial production of the induced osteogenesis product with a more marked effect.

The invention claimed is:

1. A method for preparing induced osteogenesis formulation, the method comprises the following steps order:
   (1) decalcifying two parts of dental matrix into a powder with 0.25 mm average particle diameter;
   (2) then extracting the bone morphogenetic protein (BMP) from the two parts of decalcified dental matrix powder;
   (3) finally, mixing the extracted bone morphogenetic protein with one part of the decalcified dental matrix, resulting in the induced osteogenesis formulation,
   wherein the extracting BMP step is processed in the following order:
      suspending the decalcified dental matrix powder in a phosphate buffer of pH=7.2; heating the phosphate buffer with the decalcified dental matrix powder in a water bath kettle for 280 hours, at the temperature 40° C. and simultaneously agitating the solution continuously;
      then centrifuging the solution, and separating the resulting supernatant from the precipitate; purifying and concentrating a target protein form the supernatant using a conventional molecular sieve to obtain an active BMP protein extract.

2. The method according to claim 1, wherein a molecular weight of the extracted active BMP protein is 20 to 50 kDa.

3. The method according to claim 2, wherein said binding step is performed as follows:
   firstly suspending one part of the two parts of the dental matrix powder after decalcification and protein extraction in a phosphate buffer of pH=7.0;
   then dissolving the BMP protein extracted from the two parts of dental matrix in the phosphate buffer, then mixing them together to obtain a resulting mixture; and
   putting the resulting mixture in an agitator for uniform and slow agitation at an agitation rate from 20 to 120 Rotation Per Minute, meanwhile agitated at room temperature or 25 to 30° C. for 12 to 56 hours, during agitation the concentration of the BMP protein in the mixed solution is detected every 3 hours, until the concentration decreases below 10% to 15% of initial BMP concentration and the agitation is stopped, then centrifuged, the supernatant is removed, the remaining powder is filtered, then dried at low temperature.

4. The method according to claim 1, wherein the mixing step comprises mixing the extracted BMP with one part of the dental matrix granule obtained after decalcification and extraction, and binding the BMP with the dental matrix granule.

* * * * *